(12) United States Patent
Muller et al.

(10) Patent No.: US 6,551,308 B1
(45) Date of Patent: Apr. 22, 2003

(54) LASER THERAPY ASSEMBLY FOR MUSCULAR TISSUE REVASCULARIZATION

(75) Inventors: Gerhard Muller, Berlin (DE); Kai Desinger, Berlin (DE); Brita Schaldach, Berlin (DE)

(73) Assignee: Laser-und Medizin-Technologie GmbH Berlin, Berlin (DE)

( * ) Notice: Subject to any disclaimer, the term of this patent is extended or adjusted under 35 U.S.C. 154(b) by 0 days.

(21) Appl. No.: 09/508,935

(22) PCT Filed: Aug. 7, 1998

(86) PCT No.: PCT/DE98/02320
§ 371 (c)(1),
(2), (4) Date: May 19, 2000

(87) PCT Pub. No.: WO99/13786
PCT Pub. Date: Mar. 25, 1999

(30) Foreign Application Priority Data

Sep. 17, 1997 (DE) ......... 197 40 824

(51) Int. Cl.[7] ......... A61B 18/20
(52) U.S. Cl. ......... 606/10; 606/2; 606/3; 606/13; 606/16; 604/22
(58) Field of Search ......... 606/2–19; 604/22

(56) References Cited

U.S. PATENT DOCUMENTS

| 4,469,098 A | 9/1984 | Davi |
| 4,658,817 A | 4/1987 | Hardy |
| 4,729,373 A | 3/1988 | Peyman |
| 5,390,204 A * | 2/1995 | Yessik et al. ......... 606/12 |
| 5,607,421 A | 3/1997 | Jeevanandam et al. |
| 5,702,360 A | 12/1997 | Dieras et al. |
| 5,947,957 A * | 9/1999 | Morris ......... 606/13 |

FOREIGN PATENT DOCUMENTS

| DE | 43 22 955 A1 | 1/1994 | |
| WO | 9402074 * | 2/1994 | ......... 606/10 |
| WO | WO 95/01754 | 1/1995 | |
| WO | 9635469 * | 11/1996 | ......... 606/7 |

* cited by examiner

*Primary Examiner*—David M. Shay
(74) *Attorney, Agent, or Firm*—Christie, Parker & Hale, LLP

(57) ABSTRACT

A laser therapy assembly (1) for the revascularization of muscular tissues (t), especially cardiac muscular tissue, with a laser source (2) and an optical coupling unit (9, 11) for transmitting the laser beam (L) into the muscular tissue, with an ultrasound generator (6) connected to the optical coupling unit for a transfer of heat to the muscular tissue, which can be regulated independently from the laser beam with the purpose of producing a thermal effect that can be separately adjusted, especially a marginal thermal necrosis, in a channel generated in the muscular tissue.

8 Claims, 1 Drawing Sheet

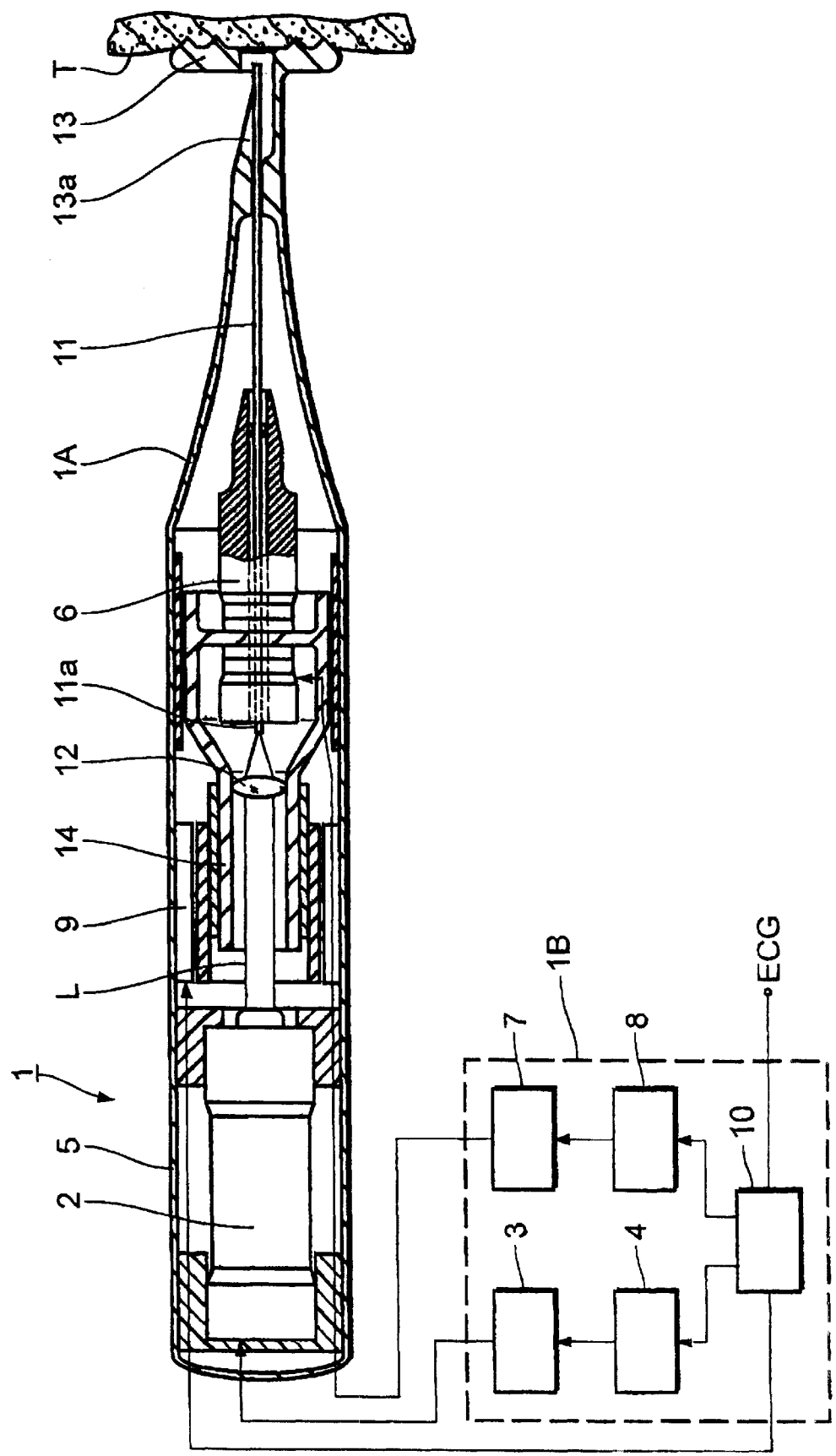

LASER THERAPY ASSEMBLY FOR MUSCULAR TISSUE REVASCULARIZATION

BACKGROUND OF THE INVENTION

The invention relates to a laser therapy assembly for revascularization of muscular tissue.

Such assemblies are known and are increasingly finding clinical application, especially in the area of cardiac surgery for the improvement of the vascularization of the cardiac muscle, especially by generating tubular necroses.

In the category of "transmyocardial laser revascularization", predominantly three different laser systems, i.e., pulsed $CO_2$ laser, pulsed holmium-YAG laser, and excimer laser are currently used to generate small perforational openings in the heart muscle, for the purpose of remedying blood circulation and supply problems in the affected muscular tissue and stimulating the formation of new vessels mid-to long-term.

Such systems are currently offered by the US companies PLC, CARDIO GENESIS, and USSC. The market prices of these systems are quite expensive.

Although obviously the mechanism which results in the improvement of the supply situation in the cardiac muscle with the use of this system is not yet understood, an at least temporary improvement of the clinical picture is observed in a relatively high percentage of the patients treated. The aforementioned laser systems vary dramatically in their adjustment parameters, with regard to wavelength and the pulse energy applicable and the pulse repetition rate, the pulse width, and the type of application; see in this regard the comprehensive presentation in the book "Transmyokardiale Laserrevascularization, Stand und Ausblicke", [Transmyocardial Laser Revascularization, State of the Art and Prospects], volume 11 of the series 'Fortschritte in der Lasermedizin' [Advances in Laser Medicine], ecomed, Landsberg and Munich, 1996.

The object of the invention is to provide a comparatively simple and economical device for revascularization of muscular tissue, especially of cardiac muscular tissue, which offers improved potentials for optimization of the treatment parameters.

The object is accomplished by means of an assembly with the characteristics reported in claim 1.

Surprisingly, it was determined that the outcomes previously achieved with the use of the aforementioned high-energy laser systems could be attributed substantially to two laser-induced effects: (1) the generation of intramuscular shock waves by the process of photoablation of a quick local thermal explosion to vaporize the tissue in the target zone as well as (2) the thermal damage to the marginal zones virtually inevitable, in principle, with this type of laser application, which—depending on the laser parameters—ranges from coagulation through carbonization to the extreme of hyperthermia.

It has now been possible to demonstrate that the previously reported acute outcomes of this process can be attributed substantially to secondary effects of the shock waves produced and pressure amplitudes associated therewith and that the long-term outcomes can be attributed substantially to the formation of the thermally affected marginal zones of the channels made by the procedure. In the prior art systems used, it is inherently impossible to optimize the action of the shock waves, i.e., the pressure amplitude generated and the duration of the shock as well as the depth of action associated therewith, separately from the marginal thermal damage occurring upon performance of the procedure. It is also impossible to further optimize the acknowledged advantageous formation of a thermal marginal zone separately from the shock waves to produce and optimize the reported long-term outcomes.

SUMMARY OF THE INVENTION

The invention includes the technical teaching, building on this knowledge, of adjusting the two effects now generated exclusively by a single laser—shock waves and marginal thermal zones—independently of each other and optimizing them patient-specifically.

Surprisingly, it further turned out that even ultrasound waves carried by optical fiber, whose basic generation is known from the patent DE-A-4,322,955 A1, can be used to generate the perforation of the muscular tissue necessary to promote vascularization. This is all the more astonishing since the prevailing opinion in the teaching assumes that ultrasound surgical devices can be used exclusively either on parenchymatous or brain tissue and to a limited extent on hard tissue, but not primarily on collagen-containing tissues, such as muscular tissue.

Within the framework of the embodiment of the invention, this problem is solved in that the working frequency of the ultrasound generator is selected in a frequency range between 20 and 100 kHz, preferably in the range between 30 and 50 kHz. Through the use of relatively high frequency ultrasound, even collagen fiber structures such as muscle tissue can be deliberately destroyed; whereby the originally athermal process of ultrasound tissue destruction can deliberately be expanded into a partially thermal process because of the increasing friction on the tissue.

Thus, not only can a fine channel be generated in the myocardium, but this channel can also be provided with an adjustable coagulation zone.

A preferred assembly consists of an either magnetostrictive or piezoelectric ultrasound oscillator, on which an amplitude transformer (a so-called ultrasonic horn) calculated according to prior art is applied to couple the optical fiber. With such a handpiece it is then possible, by application of the ultra-frequent tensile and compressive stresses to the target tissue, to rupture the tissue structure and form channels (bores) in the muscular tissue with roughly the diameter of the sound-conducting optical fiber. By active regulation of the ultrasound frequency, it is thus possible during formation of the bore to deliberately vary the impedance adaptation of the sound transmission between the sound-conducting fiber and tissue, with the result that in the event of erroneous adaptation, excess ultrasonic energy is transferred as friction loss to the channel wall and can be used there for controlled heating and thus to generate the desired marginal thermal zone.

From DE-A4,322,955, it is known that, in principle, the ultrasound oscillator to be used to couple an optical fiber can be provided with a central bore such that laser light can, in principle, also be coupled retrograde into the sound-conducting working fiber in the ultrasound handpiece by providing an additional optical fiber. This capability, which to date has been used exclusively for the transmission of continuous laser light, is now used within the framework of the invention to guide pulses of a Q-switched neodymium-YAG laser simultaneously with the transmission of sound to the distal end of the working fiber. The pulse energy of the Q-switched laser used is set such that an optical perforation can be obtained in the operating field, which results immediately in the generation of shock waves.

It is known that above this optical perforation threshold, the pressure amplitudes of the shock waves can be varied in broad ranges by increasing the laser energy. It is also known that the pulse length of a Q-switched laser can also be varied in broad ranges by active Q-switching, for example, by means of a Pockels cell. However, these measures also assume a completely different applicational aspect in their use within the framework of the invention.

Overall it can be noted that with the assembly mentioned—consisting of an ultrasound transmitter with a working fiber coupled thereto and a pulsed laser beam guided centrally by a Q-switched laser—the intended effects, i.e., the formation of a marginal thermal zone and an effective pressure wave amplitude, can be optimally adjusted separately and independently of each other.

DETAILED DESCRIPTION OF THE INVENTION

In a preferred embodiment, an optimal pulse width of the Q-switched laser is determined by preliminary testing and then the pulse amplitude or pulse energy is controlled during the treatment with a constant pulse width. For this, a passively Q-switched neodymium-YAG laser, as is known, for example, from handheld military rangefinders, is particularly well suited.

In a preferred design, the ultrasound oscillator with a coupled working fiber is installed in the interior of a cladding tube such that its axial position in the cladding tube can be altered in a controlled manner, for example, by means of an electric motor and drive with hydraulic or purely mechanical means (e.g., a spring mechanism). A miniaturized passively Q-switched neodymium-YAG laser, whose beam is then coupled by a suitable optical system through a central bore of the ultrasound oscillator into the working fiber, is flanged onto the proximal end of the cladding tube. At the distal end of the cladding tube, an attachment arrangement, by means of which the cladding tube can be temporarily affixed to the epicardium, is installed. At the time of or immediately after activation of the displacement device, the ultrasound perforation process is started with controlled advance by activation of the ultrasound oscillator and the laser.

Advantageous improvements of the invention are also characterized in the dependent claims or are presented in detail in the following along with the description of the preferred embodiment of the invention with reference to the FIGURE. This FIGURE depicts a cross-sectional view of an applicator 1 with control assemblies associated schematically in the form of a block diagram.

The entire application system 1, which consists of a handpiece 1A and a power supply and control unit 1B, is depicted. It includes a laser assembly 2 installed in the handpiece 1A with an external power supply 3 and a laser control unit 4, a cladding tube 5 forming the housing of the handpiece 1A, an ultrasound converter 6 arranged in the handpiece with an external power supply 7 and an ultrasound control unit 8, an electrical drive unit 9 in the handpiece 1A with an external drive control unit 10 and an optoacoustic optical fiber 11 coupled with the ultrasound converter 6, which transmits both the ultrasound energy generated by the ultrasound converter 6 as well as the laser energy generated by the laser assembly 2 coupled through its end surface 11a into the tissue T to be treated. A collecting lens 12 is arranged in the free beam L for optimized coupling of the laser beam.

Through a laterally open area 13a, a positioning plate 13 provided on the distal end of the handpiece with a tissue holding arrangement enables the visually supported positioning of the applicator on the tissue T. The drive unit 9 makes it possible to move the assembly consisting of the ultrasound converter 6, optical fiber 11, and collecting lens 12 affixed in a separate internal tube 14 into the tissue linearly in the axial direction controlled by the drive control unit 10 on the basis of EKG signals ECG. Depending on synchronization signals issued by the drive control unit 10 to the laser control unit 4 as well as the ultrasound control unit 8 and with the parameter settings preselected on these units, the laser assembly 2 and the ultrasound converter 6 are put in operation, and through the combined, independently controlled action of a laser-induced shock wave and primary ultrasound-induced heating, a fine channel with defined thermally modified marginal zones is generated.

Passively Q-switched neodymium-YAG lasers can be constructed with a structural size of approximately 5–8 cm length and 3–4 cm diameter, and the ultrasound oscillator is also of similar size, such that the handpiece 1A can have a structural length of approximately 15 through 25 cm with a preadjustable working thrust of the displacement device of approximately 3 cm.

The invention is not restricted in its embodiment to the above-reported preferred exemplary embodiment. Rather, a number of variants which make use of the solution presented in differently designed embodiments is possible.

Thus, a simplified embodiment has a manual process controller of the thrust of the ultrasound converter-optical fiber assembly and the activation of the laser and the ultrasound converter—preferably by means of a switch on the handpiece. Satisfactory results can also be obtained with this embodiment on the quiescent heart.

What is claimed is:

1. A laser therapy assembly for revascularizing muscular tissue, comprising:
   a laser source coupled to an optoacoustic optical fiber for transmitting a laser beam through the optoacoustic optical fiber to the muscular tissue;
   an ultrasound generator rigidly connected to the optoacoustic optical fiber for transferring heat through the optoacoustic optical fiber to the muscular tissue, the ultrasound generator being regulated independently from the laser beam to produce a thermal effect that can be separately adjusted, the laser source, the ultrasound generator, and the optoacoustic optical fiber being housed in a tube to form a handpiece;

a drive device coupled to the ultrasound generator to effect a common axial movement of both the ultrasound generator and the optoacoustic optical fiber within the handpiece; and a control unit external to the handpiece coupled to both the ultrasound generator and to the laser source for respective power control of the ultrasound generator and the laser source.

2. The laser therapy assembly according to claim 1, wherein the handpiece includes a positioning device at a handpiece end distal from the laser source for attachment to the muscular tissue and for guidance of the optoacoustic optical fiber in the common axial movement.

3. The laser therapy assembly according to claim 1, wherein the control unit includes a control device for control of the common axial movement of both the ultrasound generator and the optoacoustic optical fiber and for synchronization of the common axial movement with activation of the laser source and the ultrasound generator as a function of a heart signal.

4. The laser therapy assembly according to claim 1, wherein the laser source is a Q-switched neodymium-YAG laser whose pulse energy is adjusted such that in an operating field an optical perforation can be obtained on the muscular tissue.

5. The laser therapy assembly according to claim 1, wherein the ultrasound generator operates in the frequency range between 30 and 50 kHz.

6. The laser therapy assembly according to claim 1, wherein the ultrasound generator operates in the frequency range between 20 and 100 kHz.

7. The laser therapy assembly according to claim 1, wherein the muscular tissue is cardiac muscular tissue.

8. The laser therapy assembly according to claim 1, wherein the thermal effect that can be separately adjusted is a marginal thermal necrosis in a channel generated in the muscular tissue.

* * * * *